US006482980B1

(12) United States Patent
Dethloff et al.

(10) Patent No.: US 6,482,980 B1
(45) Date of Patent: Nov. 19, 2002

(54) PROCESS FOR PRODUCING MALEIC ACID

(75) Inventors: Christian Dethloff, Hamburg (DE); Sergio Barbarino, Naples (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/380,905

(22) PCT Filed: Mar. 6, 1998

(86) PCT No.: PCT/US98/04419

§ 371 (c)(1),
(2), (4) Date: Feb. 17, 2000

(87) PCT Pub. No.: WO98/40343

PCT Pub. Date: Sep. 17, 1998

(30) Foreign Application Priority Data

Mar. 11, 1997 (EP) ............................... 97200725

(51) Int. Cl.$^7$ ................................................ C07C 57/18
(52) U.S. Cl. ...................................................... 562/595
(58) Field of Search ......................................... 562/595

(56) References Cited

FOREIGN PATENT DOCUMENTS

JP     61-134342    *   6/1986

OTHER PUBLICATIONS

Chem Abstract Plus 1986:628907, Sugita et al, 1986.

* cited by examiner

*Primary Examiner*—Samuel Barts
(74) *Attorney, Agent, or Firm*—Armina E. Matthews; Kim William Zerby; Steven W. Miller

(57) ABSTRACT

The present invention relates to a process for producing maleic acid with close control of the temperature for optimum conversion of maleic anhydride into maleic acid and minimal production of fumaric acid.

10 Claims, 1 Drawing Sheet

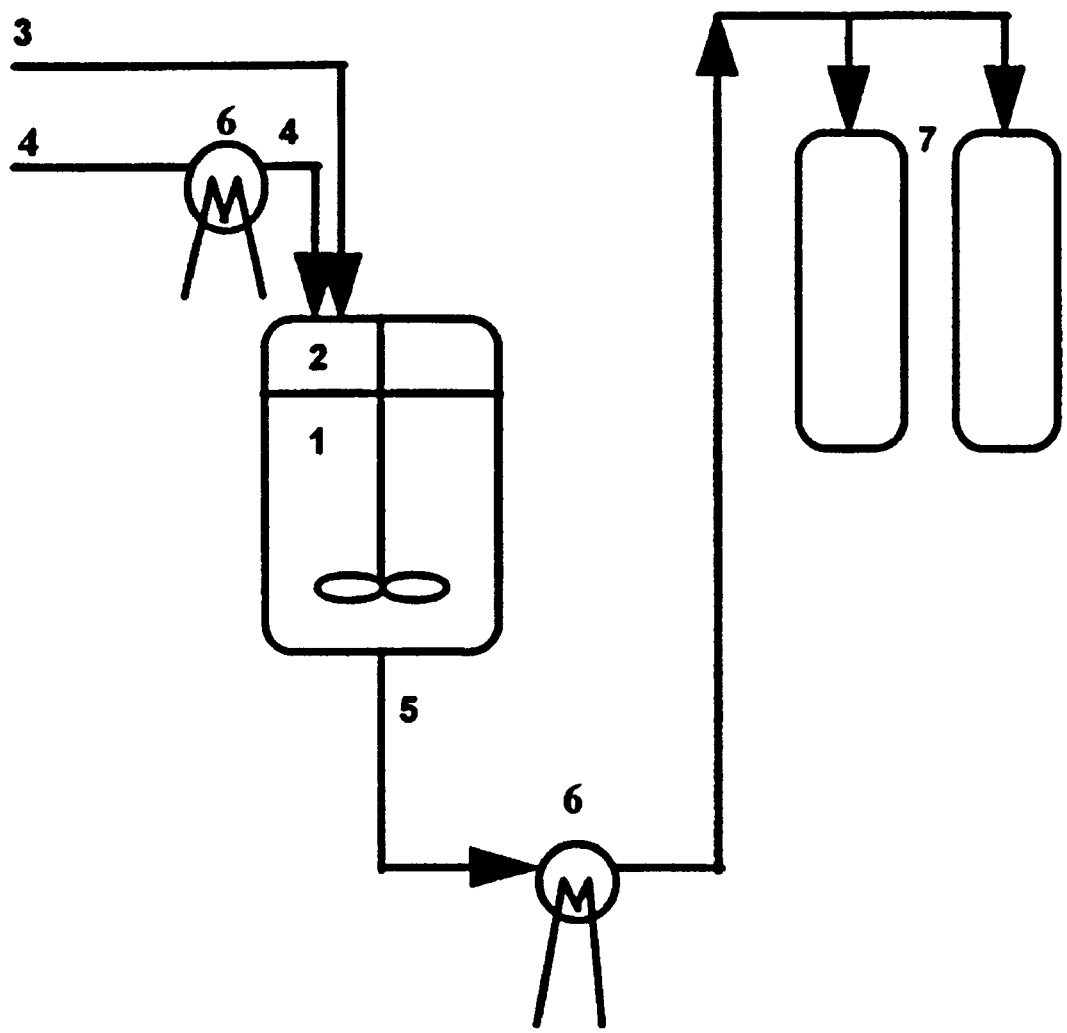

PROCESS FOR PRODUCING MALEIC ACID

FIELD OF THE INVENTION

The present invention relates to a process for producing maleic acid with minimal production of fumaric acid.

BACKGROUND OF THE INVENTION

Production of maleic acid (MA) is known in the art as being the reaction product of hydrolysis of maleic anhydride (MAH). A typical example is described in Kirk-Othmer, Encyclopedia of Chemical technology, third edition, Vol 14, page 778, wherein the process for producing MA is carried out at room temperature. The MAH is usually added in solid state. However, a problem encountered at room temperature with solid MAH is the resulting slow reaction rate. Still another problem encountered with the use of solid MAH is that it is difficult to handle when used in industrial quantities. Indeed, solid MAH is more difficult to pump, store and meter in an accurate manner compared to liquid MAH.

A solution to this problem is the production of MA in a batch, i.e. adding MAH to hot water. However, whilst this solution provides effective reaction rate, due to the exothermic reaction and resulting temperature rise, fumaric acid will also be produced in undesirable quantities as a by-product, that is higher than 0.4% by weight of the resulting reaction mixture.

Indeed, as the reaction between MAH and water is exothermic, the temperature within the reactor and thus the temperature of the reaction mixture increases. This rise in temperature favours the formation of fumaric acid instead of MA. Fumaric acid, to a certain extent, is an undesirable by-product product as it tends to precipitate at low concentrations, e.g. 0.4% by weight at room temperature. Furthermore, when incorporated in cleaning compositions, it has been found that fumaric acid compared to compositions containing MA has a lower performance towards limescale removal.

Accordingly, it is an object of the invention to provide a process with optimum conversion of MAH into MA and minimal production of fumaric acid.

It has now been surprisingly found that the use of a substantially constant temperature throughout the whole production process, that is from the contacting step of the reactants to the recovering step of the MA, fulfills such a need.

SUMMARY OF THE INVENTION

The present invention is a process for the production of maleic acid from maleic anhydride and water which comprises the steps of:
 a)-contacting maleic anhydride and water to form a reaction mixture;
 b)-recovering maleic acid from said reaction mixture; and
characterised in that said reaction mixture is maintained at a substantially constant temperature within the range of 52° C. to 85° C. during step a) and b).

BRIEF DESCRIPTION OF THE INVENTION

FIG. 1 shows a form of production unit suitable for use with the process of the invention.

DETAILED DESCRIPTION OF THE INVENTION

Starting Materials
1)—Maleic Anhydride
 MAH is an essential component for the process of the invention. MAH is preferably used in the process of the present invention in its molten form, i.e. at a temperature above 52° C. A preferred temperature of the MAH for use herein is from 55° C. to 70° C., and more preferably is 65° C.

2)—Water
 Water is another essential component for the process of the invention. Indeed, water enables the hydrolysis of the MAH into MA. Preferably, the addition of water is made in a stechiometric amount to that of the MAH. An excess amount of water is also normally used to obtain a liquid solution of MA. Typically, the water is added at a temperature of from 15° C. to 60° C. Still another advantage with the use of water in the process invention is that it may also be used as a mean to ensure that the temperature throughout the process is maintained substantially constant.

Control of the Temperature

Control of the temperature is indeed an essential feature of the invention as the reaction between MAH and water is an exothermic reaction. Indeed, if the temperature is not controlled due to the rise in temperature from the exothermic reaction, the formation of fumaric will be favoured. The Applicant has surprisingly found that applying a substantially constant temperature during the production process reaction enables the production of a high yield of maleic acid (MA) with minimal yield of fumaric acid. By high yields of maleic acid, it is meant yields of at least 99% by weight of the reaction mixture. The temperature of the reaction process during steps a) and b) should be substantially constant and within the range of from 52° C. to 85° C. The lower limit is set by the melting point of maleic anhydride. Indeed, below this temperature, MAH is in solid state which if used in such a state would result in an undesirable long reaction time, that is higher than 1 hour. On the other hand, the higher limit is set by industrial practice to avoid undesired steam. Indeed, steam may give rise to an unsafe operating process as the steam coming out and cavitating inside the pipes could then damage the pumps.

Preferably, for the purpose of the invention, the temperature throughout the process reaction is within the range of from 55° C. to 70° C., and more preferably is 65° C. By substantially constant, it is meant that the temperature should not deviate by more than 3° C. from its original value. Higher temperatures or higher temperature variations are not desired for use herein as this would lead to unacceptable yield of fumaric acid. By unacceptable yield, it is meant yield higher than 0.4% by weight. Preferably, the yield of fumaric acid should not be higher than 0.1% by weight of the resulting reaction mixture.

Control of the temperature reaction can be effected by several means such as by means of heat exchangers placed around the reaction vessel and/or by means of control of the temperature of the incoming water. Preferably, for the purpose of the invention, the control of the substantially constant temperature is effected by means of the water which is added to the process reaction. Indeed, by varying the temperature of the incoming water, control of the temperature reaction can be maintained substantially constant.

Contacting of the MAH and water involves vigorous stirring, so that intimate contact between the reactants is obtained. For a batch system, a pumping capacity of the stirrer capable of filling the reactor in a few minutes is preferred, e.g. a top entry hydrofoil or a pitched blades stirrer. However, for industrial quantities a continuous process is favoured. For reference, by industrial quantities, it is meant a reactor capacity of at least 100 kg/hour of active recovered MA, for a solution of 40% by weight in water of MA. From a mass balance point of view, this is equivalent to at least 33.6 kg/hour of incoming MAH and at least 66.3 kg/hour of incoming water. The preferred reactor for use herein has a capacity varying between 8 to 12 tons/hour, most preferably 10 tons/hour of recovered MA solution at a 40% activity by weight in water. In this instance, the stirring will depend from the pumping rate in and out of the reactor and defined so that it allows a blending time one order of magnitude higher than the pumping capacity of the reactor. For example, if the pumping capacity of the reactor in and out is of 10 t/hour, the stirring will be around 100 t/hour.

Additional means can also optionally be used to further control and/or prevent the formation of fumaric acid which can be produced as a result of the exothermic reaction between MAH and water.

One of the preferred optional means is to set a constant addition of MAH throughout the process reaction. By this constant addition, the control of the reaction temperature is simplified as only adjustments to the temperature control means, e.g. water temperature, will be required to maintain constant the reaction temperature. Such a constant addition of MAH is advantageously used in industrial processes such as continuous process as the reaction will substantially operate at steady state, that is where there is neither accumulation nor loss of mass of MA, and thereby only requiring small adjustments to the temperature control means.

Still another preferred optional means is by carrying out the process reaction in the presence of a major amount of preformed MA compared to the amount of MAH and water. By the use of such major amount of preformed MA, the side-effect of the exothermic reaction are diluted as the presence of preformed MA at start-up already provides inertia to steep temperature changes. Thus, the effects of local temperature rises from the exothermic reaction are thereby diluted. This can be achieved by the use of preformed MA which is first put in the reactor before the start of the reaction process. By major amount, it is meant a concentration that allows a reaction time of from 10 minutes to 1 hour, and preferably of 30 minutes. Typically, a concentration of preformed MA in water of 20% to 60% by weight, and preferably 35% to 45% by weight, is used; the latter being especially preferred for industrial processes. A concentration of preformed MA within the reaction mixture of 40% by weight is most preferred. The preformed MA can be purchased MA or even prepared by dissolving crystalline MAH in water. For use herein, the preformed MA is preferably set at a temperature of or above the melting point of MAH before the start of the reaction but no more than 85° C. as it would favour conversion into fumaric acid.

More preferably, the concentration of MA (i.e. produced and preformed MA) within the reaction process of the invention should be substantially constant within the reaction mixture. By substantially constant, it is meant that the concentration does not vary by more than 3%, preferably 1% of its original set value. The original set value is preferably that of the concentration for the preformed MA of from 20% to 60% by weight, preferably 35% to 45% by weight of the reaction mixture. A concentration of MA within the reaction mixture of 40% by weight is most preferred. Indeed, with such concentration the precipitation of MA in normal storage and transport conditions is avoided. Constant concentration is achieved by ensuring that upon the reaction process, there is always a steady state mass balance within the mixture, i.e. there is neither accumulation nor loss of mass of MA. Control of such steady state mass balance can be achieved using standard industrial flowmeters (e.g. Danfoss Massflowmeters), level controls (e.g. a Vega Radar LT), and control loops (e.g. PLC 5/40 Allen Bradley with operator interface on an Intouch 3.51 system). A preferred way of controlling the steady state mass balance is to set the incoming flowrates of water and MAH to their target level and control the reactor level through adjustments on the outcoming flow of the MA solution.

For the reasons described above, the MA will preferably be stored, if required, at a concentration above its solubility curve to avoid crystallisation of MA, e.g. for a concentration of 40% by weight of MA, a storage temperature of 40° C. is preferred.

As stated herein before, one of the advantage of the present process invention is that it is suitable for use as a continuous process, that is where the reactants and the products are continuously added and withdrawn. Such type of process is favoured in industrial processes as it allows continuous production of MA without having to stop the reaction. Still another advantage of such process is that it avoids long and uneconomical start-up and shut-down phases.

One of the preferred apparatus for carrying out the process of the invention is a Continuous-Flow Stirred Tank Reactor (CFSTR). CFSTR are known in the art and described in Kirk-Othmer, Encyclopedia of Chemical technology, third edition, Vol.19, pages 882–883.

CFSTR

By using the present apparatus, control of the temperature reaction, control of the constant concentration of maleic acid, as well as control of the flow rate of the reactants within the reactor can be made.

Control of the constant concentration of MA within the reactor is achieved by recovering an amount of MA of the same mass of the two incoming ones, thereby ensuring a steady state mass balance within the reactor, i.e. there is neither accumulation nor loss of mass of MA. This control is made using standard chemical engineering practice such as using standard industrial flowmeters, level controls and flow control loops as described hereinbefore.

The continuous stirred tank can also be scaled according to the desired outgoing flow rate of MA solution. By desired flow rate, it is meant that the vessel is designed so as to allow an average residence time of the reaction mixture within the reactor long enough to ensure completion of the reaction. The average residence time is given by the ratio V/F, where V is the reactor volume and F the combined volumetric flowrate of MAH and water, which is equivalent in steady state to the outgoing flow of MA. Residence times of from 10 minutes to 1 hour are preferred, most preferred is a residence time of 30 minutes.

Preferably, when producing MA industrially, a 3 step process, including the process step of the invention, is followed:

The first step is a starting step wherein a solution of preformed MA in water is added to the reactor up to the desired concentration and brought to the target temperature as hereinbefore mentioned. This step needs only to be done once in the reactor lifetime as long as enough stock of MA is kept within the reactor. The only additional step needed is at start-up after a shut-down phase where heating up of the MA solution to the set reaction temperature may be required.

The second step according to the invention is the production step which involves the addition of MAH, preferably molten, and water to the MA solution with close control of the temperature reaction, whilst at the same time a stream of MA of the same mass of the two incoming one is recovered. This recovering of MA can be achieved, for example, by using a pump (e.g. a CSF centrifugal pump) which flowrate is controlled through a control loop that maintains a constant level of MA within the reactor.

The recovered MA is stored in a tank having a storage temperature of 20° C. to 50° C. The lower limit depends on the MA solubility curve: below this temperature crystallisation of MA occurs; whilst the higher limit provides the maximum storage temperature to which the formation of fumaric acid is limited. For example, for a concentration of 40% by weight of MA in water and a maximum of 1 week storage time, a storage temperature of 40° C. is preferred.

The third step is when the production is shut down. This step involves stopping addition of the MAH and cooling the temperature reaction in the reactor from the set temperature to about 40° C. Thereafter, the reactor temperature is set to a substantially constant temperature of 40° C., like in the storage tank.

In order that the invention may be clearly understood and readily carried into effect, a preferred process according to the invention, and a form of production unit suitable for use herein, will now be described by way of example with reference to the accompanying drawing which is a flow diagram of the production unit capable of producing 10 m³/hour of a 40% by weight MA solution with a reaction temperature of 65° C. It will be appreciated by those skilled in the art that, since the drawing is diagrammatic, some conventional items of equipment such as heat exchangers, pumps, valves, vacuum equipments, temperature sensors, pressure sensors, pressure controlers, condensers, reboilers, and the like, have been omitted from the drawings for the sake of simplicity. It will be readily apparent to the skilled reader that such additional items of equipment may be necessary for the successful operation of the illustrated production unit, and the provision and positioning of such ancillary items of equipment form no part of the present invention and will be provided in accordance with standard chemical engineering practice.

Referring to the drawing, at start-up, a 40% by weight concentration of preformed MAID in water is brought to a temperature of 65° C. in a CFSTR(2) having a volume of 5 m³. Thereafter, upon production, MAH(3) at a temperature of 65° C. and water(4) at a controlled temperature of about 28° C. are added to the CFSTR (2) with stirring at a pumping rate of 1 turnaround every 3 minutes and a combined flow rate of water and MAH of 10 m³/h.

The temperature of the reaction mixture is at 65° C. by controlling the temperature of the incoming water. At the same time, an amount of MA(5) is recovered from the CFSTR(2) having the same mass of the two incoming ones. The recovered MA(5) is then passed through an heat exchanger(6) with water as a cooling fluid and brought to a temperature of 40° C. and stored in a tank(7) having a storage temperature of 40° C.

What is claimed is:

1. A process for the production of maleic acid from maleic anhydride and water which comprises the steps of:

a)-contacting maleic anhydride and water to form a reaction mixture;

b)-recovering maleic acid from said reaction mixture; and characterised in that said reaction mixture is maintained at a substantially constant temperature within the range of 52° C. to 85° C. during steps a) and b).

2. A process according to claim 1, wherein said maleic anhydride is in a molten state.

3. A process according to claim 1, wherein said reaction is started in the presence of preformed maleic acid at a concentration in water of from 20% to 60% by weight.

4. A process according to claim 3, wherein said maleic acid is at a temperature of at least the melting point of the maleic anhydride.

5. A process according to claim 1, wherein said temperature reaction is controlled by means of the water which is added to the process reaction.

6. A process according to claim 1, wherein said process is a continuous process.

7. A process according to claim 1, wherein said reaction is carried out in a continuous-flow stirred tank reactor.

8. A process according to claim 7, wherein the concentration of maleic acid within the reactor is maintained constant.

9. A process according to claim 8, wherein the concentration of maleic acid within the reactor is of from 20% to 60% by weight of the reaction mixture.

10. A process according to claim 9, wherein the reaction mixture has a residence time within the reactor of from 10 minutes to 1 hour.

\* \* \* \* \*